US008409649B2

(12) United States Patent
Ungureanu et al.

(10) Patent No.: US 8,409,649 B2
(45) Date of Patent: Apr. 2, 2013

(54) OFF-NOTE BLOCKING SENSORY ORGANIC COMPOUNDS

(75) Inventors: Ioana Maria Ungureanu, Cincinnati, OH (US); Nicole Erna Irene Brune, San Diego, CA (US); Jay Patrick Slack, Loveland, OH (US); Kimberley Gray, Loveland, OH (US); Christopher Todd Simons, Wyoming, OH (US); Jenny Ellen Evans Pennimpede, Cincinnati, OH (US)

(73) Assignee: Givaudan S.A., Bernier (CH)

( * ) Notice: Subject to any disclaimer, the term of this patent is extended or adjusted under 35 U.S.C. 154(b) by 0 days.

(21) Appl. No.: 12/593,114

(22) PCT Filed: Mar. 27, 2008

(86) PCT No.: PCT/CH2008/000135
§ 371 (c)(1),
(2), (4) Date: Sep. 25, 2009

(87) PCT Pub. No.: WO2008/119196
PCT Pub. Date: Oct. 9, 2008

(65) Prior Publication Data
US 2010/0284944 A1    Nov. 11, 2010

Related U.S. Application Data

(60) Provisional application No. 60/909,143, filed on Mar. 30, 2007, provisional application No. 60/962,515, filed on Jul. 30, 2007.

(51) Int. Cl.
*A23L 2/56* (2006.01)
*A23L 1/236* (2006.01)
*A23L 1/22* (2006.01)
*A61K 9/68* (2006.01)
*C07C 61/08* (2006.01)
*A23G 4/06* (2006.01)

(52) U.S. Cl. ........ 426/534; 426/650; 426/548; 426/590; 424/48; 562/506; 562/400

(58) Field of Classification Search .................. None
See application file for complete search history.

(56) References Cited

U.S. PATENT DOCUMENTS

| 4,457,862 | A |  | 7/1984 | Baudin et al. |
| 4,496,476 | A | * | 1/1985 | Naegeli et al. ................ 512/26 |
| 4,669,490 | A |  | 6/1987 | Naegeli et al. |
| 2002/0004092 | A1 |  | 1/2002 | Riha, III et al. |
| 2003/0035875 | A1 | * | 2/2003 | Dulebohn et al. ............ 426/548 |
| 2003/0096047 | A1 |  | 5/2003 | Riha, III et al. |
| 2004/0202619 | A1 |  | 10/2004 | Dewis et al. |
| 2006/0024335 | A1 | * | 2/2006 | Roger ............................ 424/400 |

FOREIGN PATENT DOCUMENTS

| EP | 0 073 984 A2 |   | 6/1987 |
| JP | 60 109537 A1 |   | 6/1985 |
| JP | 60109537 A | * | 6/1985 |
| WO | WO 2004/029087 |   | 4/2004 |

OTHER PUBLICATIONS

JP 60109537 A (machine translation on the japanese patent website Jun. 9, 2011).*
"Cyclopentene derivatives"; STN Database accession No. 1985:614901 abstract, 1985, Database CA [Online], Chemical Abstracts Service, Colombus, OH, US.
Arbruzov, B. A., et al. "Condensation of campholenic aldehyde with ketones and esters", STN Database accession No. 1955:49380 abstract, 1954; Database CA [Online], Chemical Abstracts Service, Columbus, OH, US.
Arbruzov, B. A., ert al: "Condensation of campholenic aldehyde with ketones and esters"; STN Database accession No. 1955:49379 abstract, 1954; Database CA [Online], Chemical Abstracts Service, Columbus, OH, US.
Hart, Barry P., et al., "Asymmetric Synthesis of the Carbapenam Core from Serine", Journal of Organic Chemistry, 2003, vol. 68, pp. 187-190.
Mousseron-Canet, M., et al., "Isomerisation photochimique dans la serie de la β-ionone", Bulletin de la Societe Chimique de France, 1963, pp. 379-383.
Nomura, Masato, et al., "Studies on the Synthetic Perfume, II. New Arome Chemicals derived from (+)-2-Pinene", Yukagaku, 1992, vol. 41, No. 4, pp. 330-335.
Ochiai, Masahito, et al., "Oxidative Grob Fragmentation of γ-Tributylstannyl Alcohols with a Combination of Iodosylbenzene, Dicyclohexylcarbodiimide, and Boron Triflouride", Journal of Organic Chemistry, 1989, vol. 54, pp. 4832-4840.
Ruzicka, Helvetica Chimica Acta, 1919, pp. 352-363.
PCT/CH2008/000135—Written Opinion of the International Searching Authority, Jul. 29, 2008.
PCT/CH2008/000135—International Search Report, Jul. 29, 2008.
GB 0720506.5—Great Britain Search Report. Feb. 28, 2008.

* cited by examiner

*Primary Examiner* — Brian Gulledge
*Assistant Examiner* — Michael P Cohen
(74) *Attorney, Agent, or Firm* — Curatolo Sidoti Co., LPA; Joseph G. Curatolo; Salvatore A. Sidoti

(57) ABSTRACT

Disclosed are compounds that block off-notes in consumables and methods of blocking off-notes in consumables including off-notes provided by artificial sweeteners including aspartame, saccharin, acesulfame K (Acesulfame potassium), sucralose and cyclamate; and including stevioside, swingle extract, glyccerhizin, perillartine, naringin dihydrochalcone, neohesperidine dihydrochalcone, mogroside V, rubusoside, rubus extract, and rebaudioside A.

12 Claims, No Drawings

000# OFF-NOTE BLOCKING SENSORY ORGANIC COMPOUNDS

CROSS REFERENCE TO RELATED APPLICATIONS

This application is a national stage application of International Application No. PCT/CH2008/000135, filed 27 Mar. 2008, which claims the benefit of U.S. Provisional Patent Application Ser. No. 60/909,143, filed 30 Mar. 2007 and U.S. Provisional Patent Application Ser. No. 60/962,515. filed 30 Jul. 2007, from which applications priority is claimed, and which are incorporated herein by reference.

TECHNICAL FIELD

Disclosed are compounds that allow to mask or block undesirable off-notes in consumables and the method of blocking off-notes employing said compounds in consumables.

SUMMARY

Provided are the following:

(1) An off-note blocking compound selected from one or more of 4-(2,2,3-trimethylcyclopent-3-enyl)but-2-enoic acid, 4-(2,2,3-trimethylcyclopentyl)butanoic acid, 4-(2,2,6-trimethylcyclohexyl)butanoic acid, 3-(2,2,6-trimethylcyclohexyl)propanoic acid, 2-(3,4-dimethylcyclohexyl)acetic acid, 2-methyl-4-(2,6,6-trimethylcyclohex-2-enyl)butanoic acid, 1-methyl-2-((1,2,2-trimethylbicyclo[3.1.0]hexan-3-yl)methyl)cyclopropanecarboxylic acid;
(E)-3-(1-(2,2,3-trimethylcyclopent-3-enyl)cyclopropyl) acrylic acid, (E)-4-(2,2,3-trimethylcyclohex-3-enyl)but-2-enoic acid, (E)-4-(2,2,3-trimethylcyclopentyl)but-3-enoic acid, (E)-4-(2,2,3-trimethylcyclopentyl)but-2-enoic acid, 1-methyl-2-((1,2,2-trimethylbicyclo[3.1.0]hexan-3-yl) methyl)cyclopropanecarboxylic acid, 2,2-dimethyl-4-(2, 2,3-trimethylcyclopentyl)butanoic acid, 2-((1,4-dimethylbicyclo[3.1.0]hexan-2-yl)methyl)-1-methylcyclopropanecarboxylic acid, 2-(1-((1,2,2-trimethylbicyclo[3.1.0]hexan-3-yl)methyl)cyclopropyl) propanoic acid, 2-(1-((1-methylbicyclo[3.1.0]hexan-2-yl) methyl)cyclopropyl)acetic acid, 3,3-dimethyl-4-(2,2,3-trimethylcyclopentyl)butanoic acid, and 4-(1-methylbicyclo[3.1.0]hexan-2-yl)butanoic acid, (E)-1-(2-(1-methylbicyclo[3.1.0]hexan-2-yl)vinyl) cyclopropanecarboxylic acid, (E)-1-(2-(7-methylspiro [2.4]heptan-4-yl)vinyl)cyclopropanecarboxylic acid, (E)-4-(1-methylbicyclo[3.1.0]hexan-2-yl)but-3-enoic acid, (E)-4-(7-methylspiro[2.4]hept-6-en-4-yl)but-2-enoic acid, (E)-4-(7-methylspiro[2.4]heptan-4-yl)but-3-enoic acid, (E)-4-(7-methylspiro[2.4]heptan-4-yl)but-2-enoic acid, (E)-4-(8-methylspiro[2.5]oct-7-en-4-yl)but-2-enoic acid, 1-(2-(7-methylspiro[2.4]heptan-4-yl)ethyl)cyclopropanecarboxylic acid, 2-((6,7-dimethylspiro[2.4]heptan-4-yl)methyl)-1-methylcyclopropanecarboxylic acid, 2-(1-((1,4-dimethylbicyclo[3.1.0]hexan-2-yl)methyl)cyclopropyl)propanoic acid, 2-(1-((1-methylbicyclo[3.1.0] hexan-2-yl)methyl)cyclopropyl)acetic acid, 2-(1-((7-methylspiro[2.4]heptan-4-yl)methyl)cyclopropyl)acetic acid, and 4-(7-methylspiro[2.4]heptan-4-yl)butanoic acid.

(2) The off-note blocking compound as described herein, including under (1), selected from one or more of 4-(2,2,3-trimethylcyclopentyl)butanoic acid, 4-(2,2,3-trimethylcyclopent-3-enyl)but-2-enoic acid, 4-(2,2,6-trimethylcyclohexyl) butanoic acid, 3-(2,2,6-trimethylcyclohexyl)propanoic acid-4-propylcyclohexanecarboxylic acid, and 2-(3,4-dimethylcyclohexyl)acetic acid.

(3) A flavor composition comprising an off-note providing consumable ingredient and one or more of the off-note blocking compounds listed herein, including under (1) and (2).

(4) A consumable comprising
  a) one or more ingredient in a concentration sufficient to provide an off-note, and
  b) one or more of the off-note blocking compounds listed herein, including under (1) and (2).

(5) A consumable as herein described, including under (4), wherein the one or more off-note providing ingredient is selected from one or more of sweetener, artificial sweetener, beverage, chewing gum, nutraceutical, and pharmaceutical.

(6) A consumable of as herein described, including under (4), wherein the one or more off-note providing ingredient is an artificial sweetener selected from one or more of aspartame, acesulfame K, saccharin, sucralose, and sodium cyclamate.

(7) A consumable as herein described, including under (4), wherein the one or more off-note providing ingredient comprises a sweetener selected from one or more of stevioside, swingle extract, glyccerhizin, perillartine, naringin dihydrochalcone, neohesperidine dihydrochalcone, mogroside V, rubusoside, rubus extract, and rebaudioside A.

(8) A consumable as herein described, including under (4), wherein the off-note providing ingredient comprises a consumable selected from one or more of cocoa, coffee, caffeine, theobromine, diketopiperazines, vitamins, amino acids, vitamin B, casein, soy protein, ibuprofen, salicylic acid, glucoronolactone, acetaminophen, dextromethorphan, naringin, taurin, macrolide (including bioxin and erythomycin), paracetamol, acetylsalicylic acid, cimetidine, ranitidine, amoxicillin, acetominophen, cephalosporines, quassia, propylene glycol, triacetin, salts of potassium, salts of zinc, loperamide, limonin, flavonoides, isoflavones (including genistein and diadzein), polyphenol (including catechin and epicatechin), mint oil, D-menthol, hydrolysed vegetable protein, bitter peptides, preservatives (including benzoic acid, potassium sorbate, polysorbate 80, sodium and potassium lactate, sodium benzoate), citric acid, quinine, urea (contained in chewing gums), essential oils (including thyme, sage, basil, mint), Maillard reaction products (including cyclic amines made from pyrrolidine/glucose, alanine/xylose, proline/sucrose or alanine/xylose, for example diketopiperazines), beer, hops, humulone, trans-isohumulone, lupulone, and hulupone.

(10) A method of blocking off-notes in a consumable comprising admixing with the consumable (a) one or more off-note providing ingredient in a concentration sufficient to provide an off-note, and (b) one or more compounds of the off-note blocking compounds listed herein, including under (1) and (2).

(11) A method as herein described, including under (10), wherein the one or more off-note providing ingredient is selected from the group consisting of sweetener, artificial sweetener, beverage, chewing gum, nutraceutical, and pharmaceutical.

(12) A method as herein described, including under (10) and (11), wherein the off-note providing ingredient comprises one or more artificial sweetener selected from aspartame, acesulfame K, saccharin, sucralose, and sodium cyclamate.

(13) A method of as herein described, including under (10) to (12), wherein the off-note providing ingredient comprises one or more sweetener selected from stevioside, swingle extract, glyccerhizin, perillartine, naringin dihydrochalcone, neohesperidine dihydrochalcone, mogroside V, rubusoside, rubus extract, and rebaudioside A.

(14) A method as herein described, including under (10) to (13), wherein the off-note providing ingredient comprises one or more consumable selected from cocoa, coffee, caffeine, theobromine, diketopiperazines, vitamins, amino acids, vitamin B, casein, soy protein, ibuprofen, salicylic acid, glucoronolactone, acetaminophen, dextromethorphan, naringin, taurin, macrolide (including bioxin and erythomycin), paracetamol, acetolsalicilic acid, cimetidine, ranitidine, amoxicillin, acetominophen, cephalosporines, quassia, propylene glycol, triacetin, salts of potassium, salts of zinc, loperamide, limonin, flavonoides, isoflavones (including genistein and diadzein), polyphenol (including catechin and epicatechin), mint oil, D-menthol, hydrolysed vegetable protein, bitter peptides, preservatives (including benzoic acid, potassium sorbate, polysorbate 80, sodium and potassium lactate, sodium benzoate), citric acid, quinine, urea (contained in chewing gums), essential oils (including thyme, sage, basil, mint), Maillard reaction products (including cyclic amines made from pyrrolidine/glucose, alanine/xylose, proline/sucrose or alanine/xylose, for example diketopiperazines), beer, hops, humulone, trans-isohumulone, lupulone, and hulupone.

DETAILED DESCRIPTION

The off-note blocking compounds provided herein include the following off-note blocking compounds: 4-(2,2,3-trimethylcyclopent-3-enyl)but-2-enoic acid, 4-(2,2,3-trimethylcyclopentyl)butanoic acid, 4-(2,2,6-trimethylcyclohexyl)butanoic acid, 3-(2,2,6-trimethylcyclohexyl)propanoic acid, 2-(3,4-dimethylcyclohexyl)acetic acid, 2-methyl-4-(2,6,6-trimethylcyclohex-2-enyl)butanoic acid, and 1-methyl-2-((1,2,2-trimethylbicyclo[3.1.0]hexan-3-yl)methyl)cyclopropanecarboxylic acid.

The chemical structures of these compounds are indicated below:

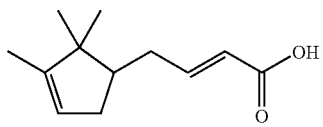

4-(2,2,3-trimethylcyclopent-3-enyl)but-2-enoic acid (including (E)-4-(2,2,3-trimethylcyclopent-3-enyl)but-2-enoic acid), and (Z)-4-(2,2,3-trimethylcyclopent-3-enyl)but-2-enoic acid)

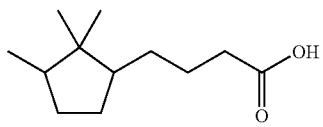

4-(2,2,3-trimethylcyclopentyl)butanoic acid

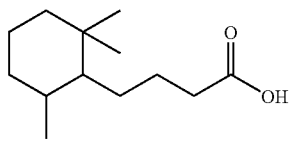

4-(2,2,6-trimethylcyclohexyl)butanoic acid

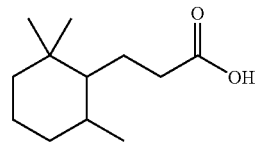

3-(2,2,6-trimethylcyclohexyl)propanoic acid

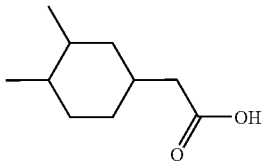

2-(3,4-dimethylcyclohexyl)acetic acid

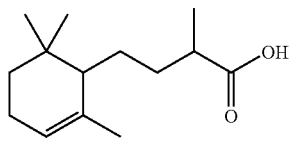 [SMILES: CC1=CCCC(C)(C)C1CCC(C)C(=O)O]

2-methyl-4-(2,6,6-trimethylcyclohex-2-enyl)butanoic acid

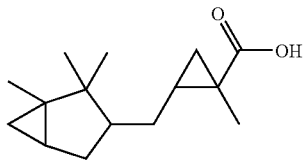 [SMILES: CC1(C(=O)O)CC1CC1CC2CC2(C)C1(C)C]

1-methyl-2-((1,2,2-trimethylbicyclo[3.1.0]hexan-3-yl)methyl)cyclopropanecarboxylic acid.

Without wishing to be bound by theory, the presence of 1 to 3 cyclopropyl groups at the 5-ring or 6-ring part of the off-note blocking compound and/or the linker linking the ring to the acid group tends to increase the off-note blocking activity. According to certain embodiments, these compounds are particularly useful for blocking the bitter off-note blocking activity. Furthermore, 5-ring structures (cyclopentane) tend to have higher activities than the related 6-ring structures (cyclohexane).

According to certain embodiments, the following groups of compounds may also be useful for off-note blocking in consumables:

One or more compound selected from (E)-3-(1-(2,2,3-trimethylcyclopent-3-enyl)cyclopropyl)acrylic acid, (E)-4-(2,2,3-trimethylcyclohex-3-enyl)but-2-enoic acid, (E)-4-(2,2,3-trimethylcyclopentyl)but-3-enoic acid, (E)-4-(2,2,3-trimethylcyclopentyl)but-2-enoic acid, 1-methyl-2-((1,2,2-trimethylbicyclo[3.1.0]hexan-3-yl)methyl) cyclopropanecarboxylic acid, 2,2-dimethyl-4-(2,2,3-trimethylcyclopentyl)butanoic acid, 2-((1,4-dimethylbicyclo[3.1.0]hexan-2-yl)methyl)-1-methylcyclopropanecarboxylic acid, 2-(1-((1,2,2-trimethylbicyclo[3.1.0]hexan-3-yl)methyl)cyclopropyl)propanoic acid, 2-(1-((1-methylbicyclo[3.1.0]hexan-2-yl)methyl)cyclopropyl)acetic acid, 3,3-dimethyl-4-(2,2,3-trimethylcyclopentyl)butanoic acid, and 4-(1-methylbicyclo[3.1.0]hexan-2-yl)butanoic acid.

The chemical structures of these compounds are shown below.

| Structure | Name |
|---|---|
|  | (E)-4-(2,2,3-trimethylcyclopentyl)but-3-enoic acid |
|  | (E)-4-(2,2,3-trimethylcyclopentyl)but-2-enoic acid |
|  | (E)-4-(2, 2, 3-trimethylcyclohex-3-enyl)but-2-enoic acid |
|  | 2,2-dimethyl-4-(2,2,3-trimethylcyclopentyl)butanoic acid |
|  | 3,3-dimethyl-4-(2,2,3-trimethylcyclopentyl)butanoic acid |
|  | 4-(1-methylbicyclo[3.1.0]hexan-2-yl)butanoic acid |
|  | 1-methyl-2-((1,2,2-trimethylbicyclo[3.1.0]hexan-3-yl)methyl)cyclopropanecarboxylic acid |
|  | 2-((1,4-dimethylbicyclo[3.1.0]hexan-2-yl)methyl)-1-methylcyclopropanecarboxylic acid |
|  | 2-(1-((1-methylbicyclo[3.1.0]hexan-2-yl)methyl)cyclopropyl)acetic acid |

-continued

| Structure | Name |
|---|---|
|  | 2-(1-((1,2,2-trimethylbicyclo[3.1.0]hexan-3-yl)methyl)cyclopropyl)propanoic acid |
|  | (E)-3-(1-(2,2,3-trimethylcyclopent-3-enyl)cyclopropyl)acrylic acid |

According to further embodiments, the following group of compounds may also be useful in off-note blocking in consumables:

(E)-1-(2-(1-methylbicyclo[3.1.0]hexan-2-yl)vinyl)cyclopropanecarboxylic acid, (E)-1-(2-(7-methylspiro[2.4]heptan-4-yl)vinyl)cyclopropanecarboxylic acid, (E)-4-(1-methylbicyclo[3.1.0]hexan-2-yl)but-3-enoic acid, (E)-4-(7-methylspiro[2.4]hept-6-en-4-yl)but-2-enoic acid, (E)-4-(7-methylspiro[2.4]heptan-4-yl)but-3-enoic acid, (E)-4-(7-methylspiro[2.4]heptan-4-yl)but-2-enoic acid, (E)-4-(8-methylspiro[2.5]oct-7-en-4-yl)but-2-enoic acid, 1-(2-(7-methylspiro[2.4]heptan-4-yl)ethyl)cyclopropanecarboxylic acid, 2-((6,7-dimethylspiro[2.4]heptan-4-yl)methyl)-1-methylcyclopropanecarboxylic acid, 2-(1-((1,4-dimethylbicyclo[3.1.0]hexan-2-yl)methyl)cyclopropyl)propanoic acid, 2-(1-((1-methylbicyclo[3.1.0]hexan-2-yl)methyl)cyclopropyl)acetic acid, 2-(1-((7-methylspiro[2.4]heptan-4-yl)methyl)cyclopropyl) acetic acid, and 4-(7-methylspiro[2.4]heptan-4-yl) butanoic acid.

The chemical structures of these compounds are shown below.

| Structure | name |
|---|---|
| 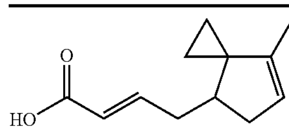 | (E)-4-(7-methylspiro[2.4]hept-6-en-4-yl)but-2-enoic acid |
| 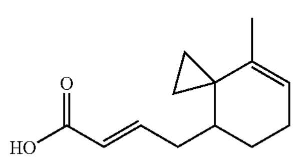 | (E)-4-(8-methylspiro[2.5]oct-7-en-4-yl)but-2-enoic acid |
| 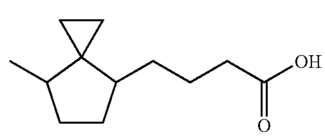 | 4-(7-methylspiro[2.4]heptan-4-yl)butanoic acid |
|  | 2-(1-((7-methylspiro[2.4]heptan-4-yl)methyl)cyclopropyl)acetic acid |

| Structure | name |
|---|---|
| | 2-(1-((1-methylbi-cyclo[3.1.0]hexan-2-yl)meth-yl)cyclopropyl) acetic acid |
| | 2-((6,7-dimethylspiro[2.4]hep-tan-4-yl)methyl)-1-methylcyclopropanecarboxylic acid |
| | 1-(2-(7-methylspiro[2.4]hep-tan-4-yl)ethyl)cyclopropane-carboxylic acid |
| | (E)-1-(2-(7-methyl-spiro[2.4]heptan-4-yl)vinyl)cyclopropane-carboxylic acid |
| | 2-(1-((1,4-dimethyl-bicyclo[3.1.0]hexan-2-yl)methyl)cyclo-propyl)propanoic acid |
| | (E)-4-(7-methylspiro[2.4]hep-tan-4-yl)but-3-enoic acid |
| | (E)-4-(7-methylspiro[2.4]hep-tan-4-yl)but-2-enoic acid |
| | (E)-4-(1-methyl-bicyclo[3.1.0]hexan-2-yl)but-3-enoic acid |
| | (E)-1-(2-(1-methyl-bicyclo[3.1.0]hexan-2-yl)vinyl)cyclopropane-carboxylic acid |

Most compounds can be synthesized easily by methods well known in the art, or as indicated below or in the examples herein.

Synthesis of 2-methyl-4-(2,6,6-trimethylcyclohex-2-enyl)butanoic acid 2-methyl-4-(2,6,6-trimethylcyclohex-2-enyl)butanoic acid can be synthesized in one step from 2-methyl-4-(2,6,6-trimethylcyclohex-2-enyl)butanal analoguously to the synthesis pathway as described by Ochiai et al. 1989, Journal of Organic Chemistry, 54(20), 4832-40.

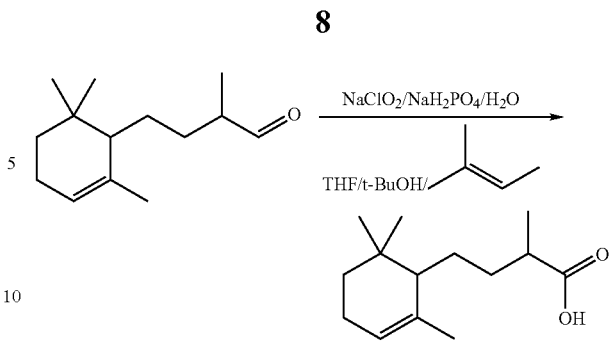

Synthesis of 2-(3,4-dimethylcyclohexyl)acetic acid 2-(3,4-dimethylcyclohexyl)acetic acid can be synthesized from 2-(3,4-dimethylphenyl)acetic acid as indicated below using hydrogen and platinumoxide ($H_2/PtO_2$) as catalyst analoguously to the synthesis pathway as described by Gault et al. (1958), Compt. rend., 246, 123-5.

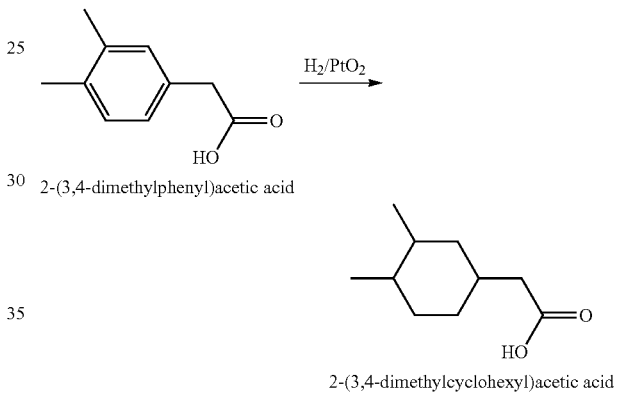

2-(3,4-dimethylphenyl)acetic acid 2-(3,4-dimethylcyclohexyl)acetic acid

Synthesis of 1-methyl-2-((1,2,2-trimethylbicyclo [3.1.0]hexan-3-yl)methyl)cyclopropanecarboxylic acid The compound can be synthesized starting from (1-methyl-2-((1,2,2-trimethylbicyclo[3.1.0]hexan-3-yl)methyl)cyclopropyl)methanol (aka Javanol®) using Ruthenium(III) chloride and sodium periodate analoguously to the synthesis pathway as described by Hart et al. 2003, Journal of Organic Chemistry 68(1), 187-190. Javanol® is commercially available from Givaudan, Vernier, Switzerland.

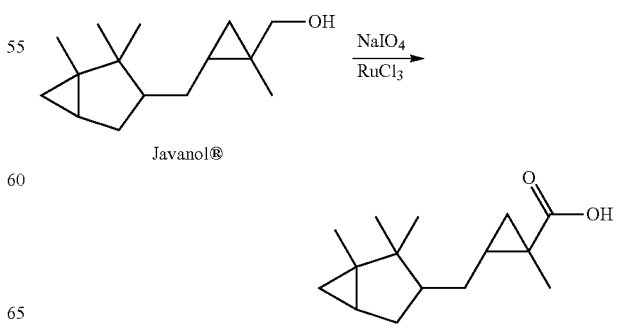

Javanol®

The synthesis of further compounds is described in examples 2a to 2d herein below. The remainder of compounds can be synthesized analogously, as will be apparent to the skilled person.

A receptor screen with concentration-response analysis was performed and from results inhibitory concentration (IC) $IC_{50}$ values can be calculated by nonlinear regression using the function $f(x)=(a-d)/(1+(x/C)^{nh})+d$; with a=minimum signal, d=maximum signal, nh=hill coefficient, $C=IC_{50}$, and x=concentration of antagonist.

$IC_{50}$ is the molar concentration of an antagonist which produces 50% of the maximum possible inhibitory response for that antagonist. A more potent antagonist will have a lower $IC_{50}$ value.

Most of the off-note blocking compounds disclosed herein, and in particular, for example, 4-(2,2,3-trimethylcyclopent-3-enyl)but-2-enoic acid, 4-(2,2,3-trimethylcyclopentyl)butanoic acid, 4-(2,2,6-trimethylcyclohexyl)butanoic acid, 3-(2,2,6-trimethylcyclohexyl)propanoic acid, 2-(3,4-dimethylcyclohexyl)acetic acid, 2-methyl-4-(2,6,6-trimethylcyclohex-2-enyl)butanoic acid, and 1-methyl-2-((1,2,2-trimethylbicyclo[3.1.0]hexan-3-yl)methyl)cyclopropanecarboxylic acid have an $IC_{50}$ in the range of about 0.1 to 20 micromolar when tested with the TAS2R44 bitter taste receptor.

For most food applications, a low $IC_{50}$ [micro molar] of 0.05 to 10 is desirable, however, $IC_{50}$ of 10 to 25 are still good and above 25 may also still acceptable depending on the application.

Various food ingredients (including ingredients naturally contained in food or additives admixed to food including flavor ingredients) provide undesirable off-notes. Particularly undesirable off-notes are the bitter off-notes, metallic off-notes, lingering, licorice-type and astringent off-notes. The term off-note refers to an unpleasant after taste that develops over time after consumption of consumables.

Other particular examples are the bitter and/or metallic and/or astringent and/or "artificial" off-notes and/or a cloyingly sweet off-note (as opposed to the "cleaner" taste of sugar) that are associated with a number of artificial sweeteners including aspartame, Ace K, saccharin, sucralose, and sodium cyclamate. Sometimes these off-notes of artificial sweeteners are described collectively as bitter off-notes.

Further examples of off-note providing ingredients are naturally occurring sweeteners including stevioside, swingle extract, glyccerhizin, perillartine, naringin dihydrochalcone, neohesperidine dihydrochalcone, mogroside V, rubusoside, rubus extract, and rebaudioside A Still further examples of off-note providing ingredients include cocoa, coffee, caffeine, theobromine, diketopiperazines, vitamins, amino acids, vitamin B, casein, soy protein, ibuprofen, salicylic acid, glucoronolactone, acetaminophen, dextromethorphan, naringin, taurin, macrolide (including bioxin and erythomycin), paracetamol, acetolsalicilic acid, cimetidine, ranitidine, amoxicillin, acetominophen, cephalosporines, quassia, propylene glycol, triacetin, potassium, zinc, loperamide, limonin, flavonoides, isoflavones (including genistein and diadzein), polyphenol (including catechin and epicatechin), mint oil, D-menthol, hydrolysed vegetable protein, bitter peptides, preservatives (including benzoic acid, potassium sorbate, polysorbate 80, sodium and potassium lactate, sodium benzoate), citric acid, quinine, urea (contained in chewing gums), essential oils (including thyme, sage, basil, mint), Maillard reaction products (including cyclic amines made from pyrrolidine/glucose, alanine/xylose, proline/sucrose or alanine/xylose, for example diketopiperazines), beer, hops, humulone, trans-isohumulone, lupulone, hulupone.

The addition of off-note blockers will block or mask the off-notes and make them less apparent or unnoticeable. Artificial sweeteners will thereby loose their bitter/metallic taste and/or their cloyingly sweet lingering sweetness and instead taste more like actual sugar (sucrose).

Aspartame is the name for aspartyl-phenylalanine-1-methyl ester, a dipeptide. It is known under various trademark names including Equal®, and Canderel®. In the European Union, it is also known under the E number (additive code) E951.

Acesulfame potassium (AceK) is the potassium salt of 6-methyl-1,2,3-oxathiazine-4(3H)-one 2,2-dioxide, an N-sulfonylamide. It is also known as Acesulfame K or AceK, or under various trademark names including Sunett® and Sweet One®. In the European Union it is also known under the E number (additive code) E950.

Saccharin is the Na salt of 1,2-Benzisothiazol-3(2H)-one, 1,1-dioxide, an N-sulfonamide. It is also known under various trademark names including Sweet'n Low®.

Sucralose is the name for 6-dichloro-1,6-dideoxy-β-D-fructo-furanosyl 4-chloro-4-deoxy-α-D-galactopyranoside, which is a chlorodeoxysugar. It is also known by the trade name Splenda®. In the European Union, it is also known under the E number (additive code) E955. Sucralose has an off-note (also designated "aftertaste") that is a lingering liquorice-like off-note sometimes also described as bitter.

The off-note blockers can be added to consumables to block the undesirable off-notes of ingredients present in said consumables or added to such consumables.

Flavor compositions for addition to consumables can be formed that provide the off-note blockers and an off-note providing ingredient for addition to consumables, and optionally food grade excipients. Alternatively, the off note blockers can be directly added to consumables.

In particular, the off-note blockers can be added to flavor compositions or directly to consumables to block the undesirable off-notes of off-note providing ingredients including natural and artificial sweeteners added to such consumables.

Consumables include all food products, food additives, nutraceuticals, pharmaceuticals and any product placed in the mouth including chewing gum, oral care products, and oral hygiene products including but not limited to, cereal products, rice products, tapioca products, sago products, baker's products, biscuit products, pastry products, bread products, confectionery products, desert products, gums, chewing gums, mouthwash, dental floss, flavored or flavor-coated straws, flavor or flavor-coated food/beverage containers, chocolates, ices, honey products, treacle products, yeast products, baking-powder, salt and spice products, savory products, mustard products, vinegar products, sauces (condiments), tobacco products, cigars, cigarettes, processed foods, cooked fruits and vegetable products, meat and meat products, jellies, jams, fruit sauces, egg products, milk and dairy products, yoghurts, cheese products, butter and butter substitute products, milk substitute products, soy products, edible oils and fat products, medicaments, beverages, carbonated beverages, alcoholic drinks, beers, soft drinks, mineral and aerated waters and other non-alcoholic drinks, fruit drinks, fruit juices, coffee, artificial coffee, tea, cocoa, including forms requiring reconstitution, food extracts, plant extracts, meat extracts, condiments, nutraceuticals, gelatins, pharmaceutical and non-pharmaceutical gums, tablets, lozenges, drops, emulsions, elixirs, syrups and other preparations for making beverages, and combinations thereof.

For example, in consumables containing potassium, the off-note blocker may be added to suppress the bitterness and the metallic off-note associated with potassium.

In coffee and cocoa products, the off-note blocker may be added to suppress the bitterness associated with caffeine, theobromine, and/or diketopiperazines present in said products.

In cheese products, in particular in enzyme-modified cheese products, the off-note blocker may be added to suppress the bitterness associated with bitter peptides present in said cheese products.

In soy products, the off-note blocker may be added to suppress the bitterness and beany off-notes associated with peptides, isoflavones such as genistein and diadzein present in said products.

In HVP (hydrolysed vegetable protein) products, the off-note blocker may be added to suppress the bitterness associated with bitter peptides present in said products.

In functional ingredients used in fortified foods, the off-note blocker may be added to suppress the bitterness associated with vitamins and amino acids present in said products.

In pharmaceuticals, the off-note blocker may be added to suppress the bitterness associated with actives or bitter additives present in said products.

In consumables containing solvents, the off-note blocker may be added to suppress the bitterness associated with propylene glycol, triacetin, or ethanol present in said products.

In citrus products, the off-note blocker may be added to suppress the bitterness associated with naringin present in said products.

In neutraceuticals and herb medicines, the off-note blocker may be added to suppress the bitterness associated with actives or additives present in said products.

In consumables containing polyphenols such as catechin and epicatechin, the off-note blocker may be added to suppress the bitterness associated with these ingredients.

In consumables containing preservatives such as potassium sorbate, polysorbate 80, sodium and potassium lactate, sodium benzoate, the off-note blocker may be added to suppress the bitterness associated with said preservatives.

In consumables containing zinc and other mineral supplements, the off-note blocker may be added to suppress the bitterness and metallic off-notes associated with said these mineral supplements.

In consumables containing mint oil or menthol (e.g. D-menthol) and citric acid of above 7%, the off-note blocker may be added to suppress the bitterness associated with this combination of ingredients.

In consumables containing quinine, the off-note blocker may be added to suppress the bitterness associated with quinine.

In consumables containing artificial sweeteners (e.g. aspartame, saccharin, acesulfameK, sucralose, cyclamate), for example beverages, a off-note blocker may be added to suppress the bitterness associated with artificial sweeteners.

In chewing gums, particular dental-type chewing gums, the off-note blocker may be added to suppress the bitterness associated with urea contained in chewing gums.

In consumables containing essential oils (e.g. thyme, sage, basil, mint), the off-note blocker may be added to suppress the bitterness associated with these essential oils.

In consumables containing vegetables or herbs or their extracts, the off-note blocker may be added to suppress the bitterness associated with these ingredients.

In consumables containing Maillard reaction products (i.e. cyclic amines made from proline/sucrose or alanine/xylose, e.g. diketopiperazines), the off-note blocker may be added to suppress the bitterness associated with Maillard reaction products.

In beer and consumables containing beer or hops, the off-note blocker may be added to suppress the bitterness associated with hops.

EXAMPLES

The following examples are set forth to describe the off-note blocking compounds in further detail and to illustrate the methods of employing the off-note blocking compounds to block or otherwise mask off-notes in consumables. The examples are illustrative and should not be construed as limiting the compounds, consumables or methods in any manner.

Example 1

Sensorial Evaluation in Various Consumables

Off-note blockers as herein described are tested by panels of 6 to 10 bitter sensitive panelists.

Panelists are asked to describe the differences in off-notes and bitter notes between the product with 0.001% (wt/wt) off-note blocker unless otherwise stated and a control without off-note blocker.

A) Aspartame/Acesulfame-K Containing Diet Energy Drink

The diet energy drink contained taurin, acesulfame K, aspartame, sucralose, glucuronolacton, caffeine, B-group vitamins (Niacin, pantothenic acid, B6, B12), aroma, sucrose, glucose, colours The sample containing the off-note blocker is found to be less bitter compared to the control.

B) Sucrose/Glucose-Sweetened Energy Drink

The diet energy drink contains taurin, glucuronolacton, caffeine, B-group vitamins (Niacin, pantothenic acid, B6, B12), aroma, sucrose, glucose, colours.

The sample containing the off-note blocker is found to have less off-notes, to be less bitter, and less astringent compared to the control.

C) Iced Low-Sugar Coffee

The sample containing the off-note blocker is found to be less bitter, and less astringent compared to the control.

D) Commercial Vanilla Flavored Nutritional Drink

Vanilla flavored nutritional drink containing calcium caseinate, soy protein isolate, sodium caseinate, vitamins and minerals.

The sample containing the off-note blocker is found to be less chalky, to have reduced protein/vitamin induced off-notes notes, and to be less astringent compared to control.

E) Saccharin Sweetened Cola Soft Drink

The sample containing the off-note blocker is found to be less bitter and to have a reduced after taste compared to the control.

F) Loperamide Containing Mint-Flavored Pharmaceutical Syrup

The syrup contained 1 mg loperamide HCl per 7.5 ml serving. The off-note blocker is used in a concentration of 0.004% (wt/wt).

The sample containing the off-note blocker is found to be less bitter with especially the lingering bitter after taste reduced.

G) Daytime Cough Syrup

The daytime cough syrup contains 325 mg acetaminophen, 10 mg dextromethorphan HBr, 5 mg phenylephrine HCl per 15 ml serving.

The sample containing the off-note blocker is found to be less bitter.

H) Dark Chocolate

The sample containing the off-note blocker is found to be less bitter.

I) Baking Chocolate (100% Cocoa, Unsweetened)

The off-note blocker is used in a concentration of 0.002% (wt/wt).

The sample containing the off-note blocker is found to be less metallic, less bitter, especially the alkaloid/caffeine-like bitterness is reduced while the upfront, warm, woody bitterness was retained.

J) Overcooked Coffee

Coffee is brewed and cooked on a burner for 3 hours. The off-note blocker is used in a concentration of 0.0005% (wt/wt).

The sample containing the off-note blocker is found to be less bitter.

K) Aspartame/Acesulfame-K Sweetened Plain Nonfat Yoghurt

The yoghurt contained 0.0193% (wt/wt) and acesulfame-K 0.0083% (wt/wt). The off-note blocker is used in a concentration of 0.00175% (wt/wt).

The sample containing the off-note blocker is found to have less off-notes compared to control.

L) Aspartame/Acesulfame-K Sweetened Cola Soft Drink

The off-note blocker is used in a concentration of 0.0063% (wt/wt).

| Cola soft drink | % (by weight) |
|---|---|
| Sodium Benzoate | 0.026 |
| Aspartame | 0.043 |
| Acesulfame-K | 0.017 |
| Caffeine | 0.011 |
| Phosphoric Acid (85%) | 0.043 |
| Citric Acid (50% cut in water) | 0.017 |
| Caramel Color | 0.085 |
| Water | Balance to 100 |

The sample containing the off-note blocker is found to have less off-notes than the control.

M) Sucralose Sweetened Cola Soft Drink

The off-note blocker is used in a concentration of 0.0035% (wt/wt).

| sucralose cola soft drink | % (by weight) |
|---|---|
| Sodium Benzoate | 0.03 |
| Sucralose (25% cut in water) | 0.06 |
| Caffeine | 0.01 |
| Phosphoric Acid (85%) | 0.08 |
| Caramel Color | 0.09 |
| Water | Balance to 100 |

The sample containing the off-note blocker is found to have less off-notes and be less bitter than the control.

Examples 2a-2xy

Synthesis of Off-Note Blocking Compounds

Example 2a

Synthesis of 4-(2,2,3-trimethylcyclopentyl)butanoic acid 4-(2,2,3-trimethylcyclopentyl)butanoic acid was synthesized in three steps; the first step reacts 2-(2,2,3-trimethylcyclopent-3-en-1-yl)acetaldehyde (aka campholenic aldehyde) to ethyl 4-(2,2,3-trimethylcyclopent-3-enyl)but-2-enoate, in the second step the latter was subjected to a hydrogenation procedure to form ethyl 4-(2,2,3-trimethylcyclopentyl)butanoic acid, and in the third step, from the latter, 4-(2,2,3-trimethylcyclopentyl)butanoic acid was formed in presence of sodium hydroxide (NaOH) and tetrahydrofuran (THF).

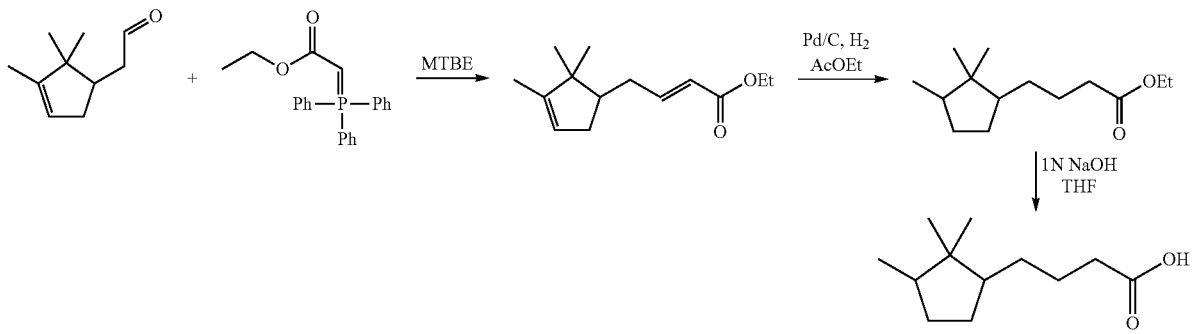

Step 1 (formation of ethyl 4-(2,2,3-trimethylcyclopent-3-enyl)but-2-enoate)

To a flame-dried 250 ml round bottom flask campholenic aldehyde (10.0 g, 65.7 mmol) and methyl tertiary-butyl ether (MTBE) (100 ml) were added to give a solution and the flask was slowly cooled to 0° C. in an ice water bath. (Carbethoxymethylene)triphenyl-phosphorane (22.8 g, 66.0 mmol) was slowly added to the solution. The reaction mixture was stirred at 0° C. for 20 min then stirred at room temperature for about 24 h. After the reaction was completed, the reaction mixture was reduced to half its volume in vacuo and 100 ml of hexanes was added. The flask containing the reaction mixture and hexanes was then placed in an ice bath for 30 min. The reaction mixture was then filtered through a plug of filter paper, celite, silica, and sand and washed three times, first with hexanes, then 9:1 and then 1:1 Hexanes/MTBE. The combined eluates were concentrated in vacuo and purifed via flash column chromatography (1:8 Hexanes/Ethyl Acetate (AcOEt)) to give ethyl 4-(2,2,3-trimethylcyclopent-3-enyl)but-2-enoate (13.1 g, 89%) as an oil. The NMR data is indicated below.

$^1$H NMR (300 MHz, CDCl3) δ 6.92 (dd, J=10.5, 7.5 Hz, 1H), 5.79 (d, J=15.6 Hz, 1H), 5.13 (s, 1H), 4.13 (m, 2H), 2.3

(m, 2H), 2.1 (m, 1H), 1.8 (m, 2H), 1.52 (s, 3H), 1.24 (t, J=15, 3H), 0.91 (s, 3H), 0.71 (s, 3H); $^{13}$C NMR (75 MHz, CDCl3) δ 166.1, 148.6, 147.8, 121.5, 121.3, 59.6, 48.9, 46.2, 35.2, 32.9, 25.5, 19.5, 14.0, 12.2; MS m/z 222.

Step 2—Hydrogenation Procedure

To a three necked round bottom flask with a stir bar flushed with nitrogen, Degussa type palladium on charcoal Pd/C (1.5 g, 10% Pd) was added as catalyst. The catalyst was covered with distilled water (8 ml) and ethyl 4-(2,2,3-trimethylcyclopent-3-enyl)but-2-enoate/ethyl 4-(2,2,3-trimethylcyclopentenyl)butanoic acid (10.0 g, 44.9 mmol) in Ethyl Acetate (AcOEt) (200 ml) was added to the reaction flask. The flask was flushed with hydrogen and the reaction was run under hydrogen balloons that were refilled as needed. After 17 h at room temperature the reaction was found to be completed by gas chromatography and mass spectrometry (GCMS). The reaction mixture was filtered through a celite plug. The organic layers were concentrated in vacuo and purified via flash column chromatography AcOEt/Hexanes (gradient 0 to 40%) to give ethyl 4-(2,2,3-trimethylcyclopentyl)butanoate/ethyl 4-(2,2,3-trimethylcyclopentyl)butanoic acid as a colorless oil (7.48 g, 74%). The NMR data is indicated below.

$^1$H NMR (300 MHz, CDCl3) δ 4.18 (q, J=7.14, 2H), 2.34 (m, 2H), 1.82 (m, 3H), 1.56 (m, 5H), 1.30 (t, J=7.2, 3H), 0. (m, 2H), 0.99 (s, 3H), 0.86 (d, J=5.4, 2H), 0.52 (s, 3H); $^{13}$C NMR (75 MHz, CDCl3) δ 173.8, 60.1, 50.6, 45.2, 42.2, 34.8, 30.1, 30.0, 28.1, 25.6, 24.3, 14.3, 14.2, 13.8; MS m/z 226.

Step 3—Saponification Reaction

Ethyl 4-(2,2,3-trimethylcyclopentyl)butanoate (5 g, 22 mmol) was added to THF (25 ml) into a round bottom flask. Aqueous 1 N NaOH (25 ml) was then added to the flask and the reaction mixture was refluxed at 110° C. for 8 h. Upon completion of the reaction, the reaction mixture was diluted with 1 N NaOH (25 ml) and the aqueous layer washed twice with MTBE (50 ml×2). The aqueous layer was treated with aqueous 1.0 N HCl until it reached a pH of about 3 (for example from 2 to 4), then extracted three times with AcOEt (50 ml×3). The combined AcOEt extracts were concentrated in vacuo and purified via flash column chromatography with (0-40% gradient) to give 4-(2,2,3-trimethylcyclopentyl)butanoic acid as a colorless oil (3.82 g, 87%). The NMR data is indicated below.

$^1$H NMR (300 MHz, CDCl3) δ 11.22 (br s, 1H), 2.37 (m, 2H), 1.75 (m, 3H), 1.49 (m, 4H), 1.17 (m, 3H), 0.86 (s, 3H), 0.84 (d, J=6.9 Hz, 3H), 0.52 (s, 3H); $^{13}$C NMR (75 MHz, CDCl3) δ 179.9, 50.6, 45.2, 42.2, 34.4, 30.1, 30.0, 28.1, 25.0, 24.0, 14.3, 13.8; MS m/z 198.

Example 2b

Synthesis of 4-(2,2,3-trimethylcyclopent-3-enyl)but-2-enoic acid 4-(2,2,3-trimethylcyclopent-3-enyl)but-2-enoic acid was synthesized in two steps; the first step reacts campholenic aldehyde to ethyl 4-(2,2,3-trimethylcyclopent-3-enyl)but-2-enoate as described herein-above, and in the second step, from the latter, 4-(2,2,3-trimethylcyclopent-3-enyl)but-2-enoic acid was formed in presence of NaOH and THF (see reaction below).

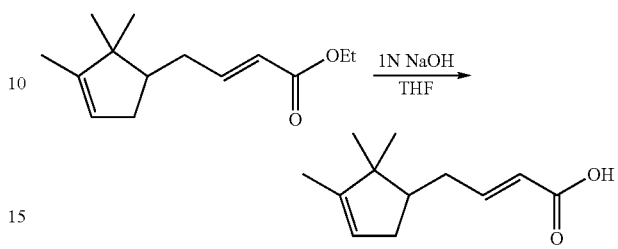

Ethyl 4-(2,2,3-trimethylcyclopent-3-enyl)but-2-enoate (2.0 g, 9.0 mmol) was added to THF (10 ml) in a 50 ml round bottom flask. Aqueous 1 N NaOH (10 ml) was then added to the flask and the reaction mixture was refluxed at 83° C. for 19 h. Upon completion of the reaction, the reaction mixture was diluted with 1 N NaOH (10 ml) and the aqueous layer was washed twice with MTBE (10 ml×2). The aqueous layer was treated with aqueous 1.0 N HCl until it reached a pH of about 3 (for example from 2 to 4), then extracted three times with AcOEt (10 ml×3). The combined AcOEt extracts were concentrated in vacuo and purified via flash column chromatography with MTBE/Hexanes (5-20% gradient) to give 4-(2,2,3-trimethylcyclopent-3-enyl)but-2-enoic acid (1.58 g) as a viscous oil (1.58 g, 90%). The NMR data is indicated below.

$^1$H NMR (300 MHz, CDCl3) δ 11.47 (br. s, 1H), 7.15 (m, 1H), 5.90 (d, J=2.8 Hz 1H), 5.23 (s, 1H), 2.39 (m, 3H), 1.91 (m, 2H), 1.62 (s, 3H), 1.20 (s, 3H), 0.827 (s, 3H); $^{13}$C NMR (75 MHz, CDCl3) δ 171.3, 152.2, 148.3, 121.9, 120.9, 49.1, 46.9, 35.4, 33.4, 25.8, 19.7, 12.5; MS m/z 194.

Example 2c

Synthesis of 4-(2,2,6-trimethylcyclohexyl)butanoic acid 4-(2,2,6-trimethylcyclohexyl)butanoic acid was synthesized in three steps starting from 2-(2,6,6-trimethylcyclohex-1-enyl)acetaldehyde, analogous to the 3-step procedure described for 4-(2,2,3-trimethylcyclopentyl)butanoic acid herein-above, with the exception that AcOEt was replaced by methanol (MeOH) in step 2, as indicated below. The first step forms (E)-ethyl 4-(2,6,6-trimethylcyclohex-1-enyl)but-2-enoate, the second step forms ethyl 4-(2,2,6-trimethylcyclohexyl)butanoate, the third forms 4-(2,2,6-trimethylcyclohexyl)butanoic acid. The majority of the product comprises (E)-4-(2,2,3-trimethylcyclopent-3-enyl)but-2-enoic acid), and (Z)-4-(2,2,3-trimethylcyclopent-3-enyl)but-2-enoic acid) is present in a concentration of up to 10% (w/w) in the isomeric mixture.

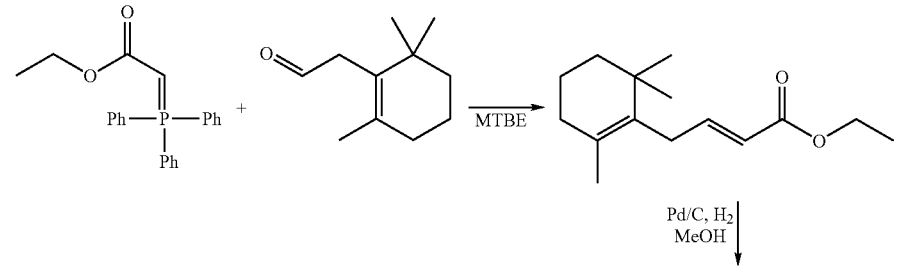

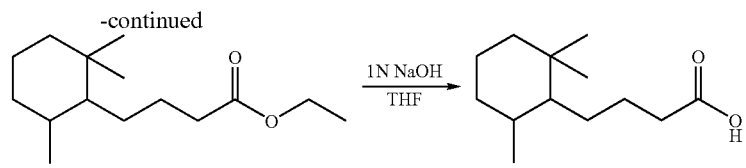

Example 2d

Synthesis of 3-(2,2,6-trimethylcyclohexyl)propanoic acid 3-(2,2,6-trimethylcyclohexyl)propanoic acid was synthesized in three steps starting from 2,6,6-trimethylcyclohex-1-enecarbaldehyde, analogous to the 3-step procedure described for 4-(2,2,6-trimethylcyclohexyl)butanoic acid and 4-(2,2,3-trimethylcyclopentyl)butanoic acid herein-above, as indicated below.

The first step formed (E)-ethyl 3-(2,6,6-trimethylcyclohex-1-enyl)acrylate, the second step formed ethyl 3-(2,2,6-trimethylcyclohexyl)propanoate, the third formed the product 3-(2,2,6-trimethylcyclohexyl)propanoic acid.

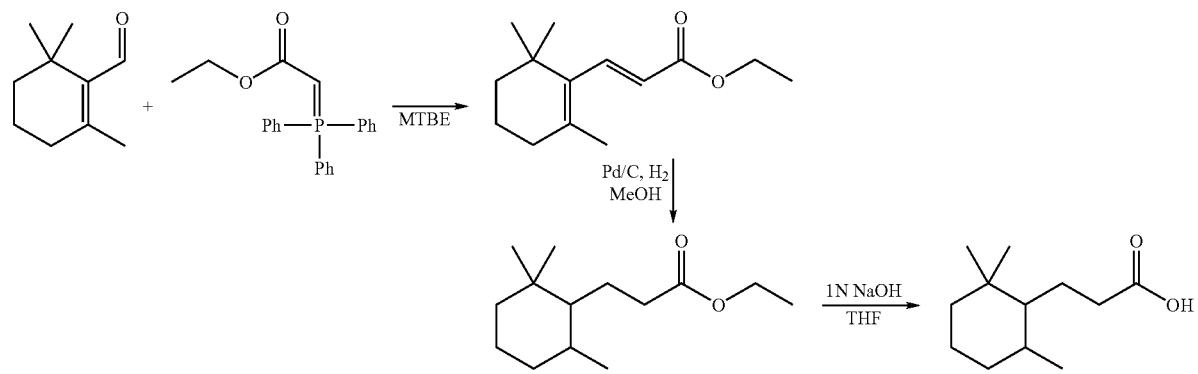

Example 3

TAS2R44 Bitter Taste Receptor Assay for IC 50 Determination

1) Generation of human TAS2R44 expression vector

The full length gene of human TAS2R44 was amplified by polymerase chain reaction (PCR) using gene-specific primers that span the entire coding region as described in WO 2004/029087.

The TAS2R44 cDNA was subcloned into an expression cassette based on either of the following plasmids/expression vectors: pcDNA3.1Zeo (Invitrogen). These vectors contain within their multiple cloning sites the nucleotide sequence coding for the first 45 amino acids of the rat somatostatin receptor subtype 3 (RSS tag) to facilitate cell surface targeting of the transgene (SEQ ID #4) and the nucleotide sequence coding for the herpes simplex virus (HSV) glycoprotein D epitope (HSV epitope in aminoterminal to carboxyterminal direction, HSV tag). (SEQ ID #3) for facilitating immunocytochemical detection.

The TAS2R44 construct contains RSS tag, TAS2R44, and the HSV tag which are fused in frame to allow translation into the receptor protein and the resulting receptor cDNA. This transfected expression vector is called pcDNA3.1Zeo-TAS2R44 (SEQ ID #1) and allows for expression of the TAS2R44 protein (SEQ ID #2).

2) Generation of a cell line stably expressing Gα16-gustducin44 and TAS2R44

A cell line that stably expresses the human bitter taste receptor (TAS2R44) was generated by transfecting pcDNA3.1Zeo-TAS2R44 into HEK293T/Gα16-gustducin 44 cells (both formed as described in under 1) above. The host cell line HEK-293T is commercially available from the American Tissue Culture Collection (catalog #CRL-1573). Transfection was performed as follows:

On day 0, the HEK293T Gα16-gustducin44 cells were seeded in a 6-well plate at a density of 900,000 cells per well and grown over night in selective growth medium (DMEM with 10% (v/v) heat-inactivated fetal bovine serum, 2 mM L-glutamine, 100 units/ml penicilin, 100 µg/ml streptomycin, 200 µg/ml G418 and 200 µg/ml zeocin).

On day 1, the medium was exchanged with 2 ml of antibiotic-free and serum-free growth medium. 10 µl Lipofectamine 2000 was dissolved in 250 µl DMEM and incubated for 5 minutes at room temperature. In parallel, 4 µg TAS2R44 vector DNA were dissolved in 250 µl DMEM. These two resulting solutions are mixed and incubated for 20 minutes at room temperature before they are added to the cells into the cell culture medium. After 4 hours, the medium is replaced with antibiotic-free, serum-containing growth medium. The cells were incubated in humidified atmosphere (37° C., 5% $CO_2$).

After 24 hours, the cells were re-plated in selective growth medium and were further incubated in a humidified atmosphere (37° C., 5% $CO_2$).

After 2 to 4 weeks of culture (replacing medium as necessary), zeocin-resistant colonies were selected and expanded.

The selected clone was tested successfully for functional expression of TAS2R44.

3) Fluo-4 Calcium Assay

Fluo-4 AM (Invitrogen) is a fluorescent indicator of intracellular calcium dynamics (change in concentration) and allows monitoring changes in the calcium concentration, particularly an increase in response to receptor activation occurring after agonist exposure.

At day 0, the HEK293T cell line stably expressing Gα16-gustducin44 and TAS2R44 formed as described under 2) was seeded in antibiotic-free growth medium (standard DMEM with 10% (v/v) heat-inactivated fetal bovine serum, 2 mM L-glutamine standard DMEM with 10% (v/v) heat-inactivated fetal bovine serum, 2 mM L-glutamine, 100 units/ml penicillin, and 100 µg/ml streptomycin) into black wall/clear bottom 96-well plates, coated with poly(ethylenimine) (0.005% v/v) at a concentration of 15,000 cells per well and incubated for 48 hours in humidified atmosphere (37° C., 5% $CO_2$).

At the time of the assay, the growth medium was discarded and the cells were further incubated in a humidified atmosphere (37° C., 5% $CO_2$) for 1 hour with 50 µl of loading buffer consisting of 1.5 µM Fluo-4 AM and 2.5 µM probenicid (Sigma-Aldrich) in DMEM.

Afterwards, the 96-well plate was washed 5 times with 200 µl of assay buffer (130 mM NaCl, 5 mM KCl, 10 mM HEPES, 2 mM $CaCl_2$, and 5 mM dextrose, pH 7.4) per well, using an automated plate washer (BioTek). The plate was further incubated for 30 minutes at room temperature in the dark to allow for complete de-esterification of the Fluo-4. Afterwards the plate was washed 5 times with 200 µl of assay buffer per well, and reconstituted with 180 µl of assay buffer per well.

For assay reading, the plate was placed in a Fluorometric Imaging Plate Reader (FLIPR) (FLIPR-TETRA™, Molecular Devices), and receptor activation was initiated by addition of 20 µl of a tenfold concentrated agonist stock solution (to give the desired agonist end concentration when added to the 180 microliter assay buffer volume), which was prepared in assay buffer.

Fluorescence was continuously monitored for 20 seconds to give a signal baseline (averaged to give $F_0$) prior to agonist addition and for 120 seconds after agonist addition. The change in signal divided by $F_0$ gives $\Delta F/F_0$ indicated in the table, with AF being the maximum signal occurring within the 120 seconds minus the minimum signal (occurring within the 120 seconds after agonist addition.

All data was collected from at least two independent experiments each carried out in triplicate.

A concentration-response analysis was performed and $IC_{50}$ values were calculated by nonlinear regression using the function $f(x)=(a-d)/(1+(x/C)^{nh})+d$; with a=minimum signal, d=maximum signal, nh=hill coefficient, $C=IC_{50}$, and x=antagonist concentration. $IC_{50}$ is the molar concentration of an antagonist which produces 50% of the maximum possible effective/inhibitory response for that antagonist. A more potent antagonist will have a lower $IC_{50}$ value.

The obtained calcium signals were corrected for the response of cells expressing only the G Protein α subunit (Gα16-gustducin44) and normalized to the fluorescence of cells prior to the stimulus using $\Delta F/F0$ (Fmax-Fmin/F0).

Example 4

Determination of IC50 of Off-Note Blockers, Saccharin

The following off-note blockers were tested: 4-(2,2,3-trimethylcyclopentyl)butanoic acid, 4-(2,2,6-trimethylcyclohexyl)butanoic acid, 3-(2,2,6-trimethylcyclohexyl)propanoic acid, 2-(3,4-dimethylcyclohexyl)acetic acid, 2-methyl-4-(2,6,6-trimethylcyclohex-2-enyl)butanoic acid, and 1-methyl-2-((1,2,2-trimethylbicyclo[3.1.0]hexan-3-yl)methyl)cyclopropanecarboxylic acid.

The method was performed as described in example 3, using saccharin as agonist. The cells are exposed to a constant concentration of saccharin (0.5 mM) and to a set of different concentrations of the off-note blocker. A fluo-4 calcium assay was performed as described above in example 3 and gave an $IC_{50}$ [micro molar] within the range of 0.05 to 25.

This means that the off-note blockers inhibited the response of the TAS2R44 bitter taste receptor and will be useful to block bitter taste.

Example 5

Determination of IC50 for Off-Note Blockers, Acesulfame K

The method was performed as described in example 4, exchanging saccharin for Acesulfame K (0.8 mM) as agonist. An $IC_{50}$ within the same range was determined. This means that the off-note blockers inhibited the response of the TAS2R44 bitter taste receptor and will be useful to block bitter taste.

Example 6

Determination of IC50 for Off-Note Blockers, Sucralose

The method was performed testing 4-(2,2,3-trimethylcyclopent-3-enyl)but-2-enoic acid as described in example 4, exchanging saccharin for sucralose (50 mM) as agonist. An $IC_{50}$ within the same range was determined. This means that the off-note blockers inhibited the response of the TAS2R44 bitter taste receptor and will be useful to block bitter taste.

Example 7

Sensory Evaluation of 4-(2,2,3-trimethylcyclopent-3-enyl)but-2-enoic acid

The bitter blocker (13 ppm) was tested in water with sucralose in concentrations of 1 mM, 3 mM, and 7 mM by a panel of bitter sensitive individuals (15) in two replications per each concentration. The samples were compared to negative controls without bitter blocker and panelists were instructed to choose the less bitter sample in a forced choice test.

The bitter blocker was found to significantly reduce bitterness (22/30 panelists chose the sample with bitter blocker as less bitter).

The sequences employed in the constructs and methods described-herein can be found in the sequence listing hereinbelow.

While the compounds, consumable and methods have been described above in connection with illustrative embodiments, it is to be understood that other similar embodiments may be used or modifications and additions may be made to the described embodiments for performing the same function without deviating therefrom. Further, all embodiments disclosed are not necessarily in the alternative, as various embodiments of the invention may be combined to provide the desired characteristics. Variations can be made by one having ordinary skill in the art without departing from the spirit and scope of the invention. Therefore, the compounds, consumables and methods should not be limited to any single embodiment, but rather construed in breadth and scope in accordance with the recitation of the attached claims.

The invention claimed is:

1. An off-note blocking compound, wherein the compound is 4-(2,2,3-trimethylcyclopentyl)butanoic acid.

2. A flavor composition comprising an off-note providing consumable ingredient and one or more off-note blocking compounds selected from 4-(2,2,3-trimethylcyclopentyl)butanoic acid, 4-(2,2,6-trimethylcyclohexyl)butanoic acid, 3-(2,2,6-trimethylcyclohexyl)propanoic acid, 2-(3,4-dimethylcyclohexyl)acetic acid, 2-methyl-4-(2,6,6-trimethylcyclohex-2-enyl)butanoic acid, 1-methyl-2-((1,2,2-trimethylbicyclo[3.1.0]hexan-3-yl)methyl)cyclopropanecarboxylic acid; (E)-3-(1-(2,2,3-trimethylcyclopent-3-enyl)cyclopropyl) acrylic acid, (E)-4-(2,2,3-trimethylcyclohex-3-enyl)but-2-enoic acid, (E)-4-(2,2,3-trimethylcyclopentyl)but-3-enoic acid, (E)-4-(2,2,3-trimethylcyclopentyl)but-2-enoic acid, 1-methyl-2-(1,2,2-trimethylbicyclo[3.1.0]hexan-3-yl)methyl)cyclopropanecarboxylic acid, 2,2-dimethyl-4-(2,2,3-trimethylcyclopentyl)butanoic acid, 2-((1,4-dimethylbicyclo[3.1.0]hexan-2-yl)methyl)-1-methylcyclopropanecarboxylic acid, 2-(1-((1,2,2-trimethylbicyclo[3.1.0]hexan-3-yl)methyl)cyclopropyl)propanoic acid, 2-(1-((1-methylbicyclo[3.1.0]hexan-2-yl)methyl)cyclopropyl)acetic acid, 3,3-dimethyl-4-(2,2,3-trimethylcyclopentyl)butanoic acid, and 4-(1-methylbicyclo[3.1.0]hexan-2-yl)butanoic acid, (E)-1-(2-(1-methylbicyclo[3.1.0]hexan-2-yl)vinyl) cyclopropanecarboxylic acid, (E)-1-(2-(7-methylspiro[2.4]heptan-4-yl)vinyl)cyclopropanecarboxylic acid, (E)-4-(1-methylbicyclo[3.1.0]hexan-2-yl)but-3-enoic acid, (E)-4-(7-methylspiro[2.4]hept-6-en-4-yl)but-2-enoic acid, (E)-4-(7-methylspiro[2.4]heptan-4-yl)but-3-enoic acid, (E)-4-(7-methylspiro[2.4]heptan-4-yl)but-2-enoic acid, (E)-4-(8-methylspiro[2.5]oct-7-en-4-yl)but-2-enoic acid, 1-(2-(7- methylspiro[2.4]heptan-4-yl)ethyl)cyclopropanecarboxylic acid, 2-((6,7-dimethylspiro[2.4]heptan-4-yl)methyl)-1-methylcyclopropanecarboxylic acid, 2-(1-((1,4-dimethylbicyclo[3.1.0]hexan-2-yl)methyl)cyclopropyl)propanoic acid, 2-(1-((1-methylbicyclo[3.1.0]hexan-2-yl)methyl)cyclopropyl)acetic acid, 2-(1-((7-methylspiro[2.4]heptan-4-yl)methyl)cyclopropyl)acetic acid, and 4-(7-methylspiro[2.4]heptan-4-yl)butanoic acid.

3. A consumable comprising
a) one or more ingredient in a concentration sufficient to provide an off-note, and
b) one or more off-note blocking compounds selected from 4-(2,2,3-trimethylcyclopentyl)butanoic acid, 4-(2,2,6-trimethylcyclohexyl)butanoic acid, 3-(2,2,6-trimethylcyclopentyl)butanoic acid, 2-(3,4-dimethylcyclohexyl)acetic acid, 2-methyl-4-(2,6,6-trimethylcyclohex-2-enyl)butanoic acid, 1-methyl-2-((1,2,2-trimethylbicyclo[3.1.0]hexan-3-yl)methyl)cyclopropanecarboxylic acid, (E)-3-(1-(2,2,3-trimethylcyclopent-3-enyl)cyclopropyl)acrylic acid, (E)-4-(2,2,3-trimethylcyclohex-3-enyl)but-2-enoic acid, (E)-4-(2,2,3-trimethylcyclopentyl)but-3-enoic acid, (E)-4-(2,2,3-trimethylcyclopentyl)but-2-enoic acid, 1-methyl-2-(1,2,2-trimethylbicyclo[3.1.0]hexan-3-yl)methyl)cyclopropanecarboxylic acid, 2,2-dimethyl-4-(2,2,3-trimethylcyclopentyl)butanoic acid, 2-((1,4-dimethylbicyclo[3.1.0]hexan-2-yl)methyl)-1-methylcyclopropanecarboxylic acid, 2-(1-((1,2,2-trimethylbicyclo[3.1.0]hexan-3-yl)methyl)cyclopropyl)propanoic acid, 2-(1-((1-methylbicyclo[3.1.0]hexan-2-yl)methyl)cyclopropyl)acetic acid, 3,3-dimethyl-4-(2,2,3-trimethylcyclopentyl)butanoic acid, and 4-(1-methylbicyclo[3.1.0]hexan-2-yl)butanoic acid, (E)-1-(2-(1-methylbicyclo[3.1.0]hexan-2-yl)vinyl)cyclopropanecarboxylic acid, (E)-1-(2-(7-methylspiro[2.4]heptan-4-yl)vinyl)cyclopropanecarboxylic acid, (E)-4-(1-methylbicyclo[3.1.0]hexan-2-1 but-3-enoic acid (E)-4-(7-methylspiro[2.4]hept-6-en-4-yl)but-2-enoic acid, (E)-4-(7-methylspiro[2.4]heptan-4-yl)but-3-enoic acid, (E)-4-(7-methylspiro[2.4]heptan-4-yl)but-2-enoic acid, (E)-4-(8-methylspiro[2.5]oct-7-en-4-yl)but-2-enoic acid, 1-(2-(7-methylspiro[2.4]heptan-4-yl)ethyl)cyclopropanecarboxylic acid, 2-((6,7-dimethylspiro[2.4]heptan-4-yl)methyl)-1-methylcyclopropanecarboxylic acid, 2-(1-((1,4-dimethylbicyclo[3.1.0]hexan-2-yl)methyl)cyclopropyl)propanoic acid, 2-(1-((1-methylbicyclo[3.1.0]hexan-2-yl)methyl)cyclopropyl)acetic acid, 2-(1-((7-methylspiro[2.4]heptan-4-yl)methyl)cyclopropyl)acetic acid, and 4-(7-methylspiro[2.4]heptan-4-yl)butanoic acid.

4. The consumable of claim 3, wherein the one or more off-note providing ingredient is selected from the group consisting of sweetener, artificial sweetener, beverage, chewing gum, nutraceutical, and pharmaceutical.

5. The consumable of claim 3, wherein the one or more off-note providing ingredient comprises an artificial sweetener selected from the group consisting of aspartame, Acesulfame K, saccharin, sucralose, sodium cyclamate and mixtures thereof.

6. The consumable of claim 3, wherein the one or more off-note providing ingredient comprises a sweetener selected from the group consisting of stevioside, swingle extract, glycyrrhizin, perillartine, naringin dihydrochalcone, neohesperidine dihydrochalcone, mogroside V, rubusoside, rubus extract, rebaudioside A and mixtures thereof.

7. The consumable of claim 3, wherein the one or more off-note providing ingredient comprises a consumable selected from the group consisting of cocoa; coffee; caffeine; theobromine; diketopiperazines; vitamins; amino acids; vitamin B; casein; soy protein; ibuprofen; salicylic acid; glucoronolactone; acetaminophen; dextromethorphan; naringin; taurine; macrolide; bioxin; erythromycin; paracetamol; acetylsalicylic acid; cimetidine; ranitidine; amoxicillin; cephalosporins; quassia; propylene glycol; triacetin; potassium; zinc; loperamide; limonin; flavonoids; isoflavones; genistein; diadzein; polyphenol; catechin; epicatechin; mint oil; D-menthol; hydrolysed vegetable protein; bitter peptides; preservatives; benzoic acid; potassium sorbate; polysorbate 80; sodium lactate; potassium lactate; sodium benzoate; citric acid; quinine; urea contained in chewing gums; essential oils; thyme; sage; basil; mint; Maillard reaction products; cyclic amines made from pyrrolidine/glucose, alanine/xylose, proline/sucrose or alanine/xylose; beer; hops; humulone; trans-isohumulone; lupulone; hulupone; and mixtures thereof.

8. A method of blocking off-notes in consumables comprising: admixing with the consumable (a) one or more off-note providing ingredient in a concentration sufficient to provide an off-note, and (b) one or more off-note blocking compound selected from of 4-(2,2,3-trimethylcyclopentyl)butanoic acid, 4-(2,2,6-trimethylcyclohexyl)butanoic acid, 3-(2,2,6-trimethylcyclohexyl)propanoic acid, 2-(3,4-dimethylcyclohexyl)acetic acid, 2-methyl-4-(2,6,6-trimethylcyclohex-2-enyl)butanoic acid, 1-methyl-2-((1,2,2-trimethylbicyclo[3.1.0]hexan-3-yl)methyl)cyclopropanecarboxylic acid, (E)-3-(1-(2,2,3-trimethylcyclopent-3-enyl)cyclopropyl) acrylic acid, (E)-4-(2,2,3-trimethylcyclohex-3-enyl)but-2-enoic acid, (E)-4-(2,2,3-trimethylcyclopentyl)but-3-enoic acid, (E)-4-(2,2,3-trimethylcyclopentyl)but-2-enoic acid, 1-methyl-2-(1,2,2-trimethylbicyclo[3.1.0]hexan-3-yl)methyl)cyclopropanecarboxylic acid, 2,2-dimethyl-4-(2,2,3-trimethylcyclopentyl)butanoic acid, 2-((1,4-dimethylbicyclo[3.1.0]hexan-2-yl)methyl-1-methylcyclopropanecarboxylic acid, 2-(1-((1,2,2-trimethylbicyclo[3.1.0]hexan-3-yl)methyl)cyclopropyl)propanoic acid, 2-(1-((1-methylbicyclo[3.1.0]hexan-2-yl)methyl)cyclopropyl)acetic acid, 3,3-dimethyl-4-(2,2,3-trimethylcyclopentyl)butanoic acid, and 4-(1-methylbicyclo[3.1.0]hexan-2-yl)butanoic acid, (E)-1-(2-(1-methylbicyclo[3.1.0]hexan-2-yl)vinyl)cyclopropanecarboxylic acid, (E)-1-(2-(7-methylspiro[2.4]heptan-4-yl)vinyl)cyclopropanecarboxylic acid, (E)-4-(1-methylbicyclo[3.1.0]hexan-2-1 but-3-enoic acid (E)-4-(7-methylspiro[2.4]hept-6-en-4-yl)but-2-enoic acid, (E)-4-(7-methylspiro[2.4]heptan-4-yl)but-3-enoic acid, (E)-4-(7-methylspiro[2.4]heptan-4-yl)but-2-enoic acid, (E)-4-(8-methylspiro[2.5]oct-7-en-4-yl)but-2-enoic acid, 1-(2-(7-methylspiro[2.4]heptan-4-yl)ethyl)cyclopropanecarboxylic acid, 2-((6,7-dimethylspiro[2.4]heptan-4-yl)methyl)-1-methylcyclopropanecarboxylic acid, 2-(1-((1,4-dimethylbicyclo[3.1.0]hexan-2-yl)methyl)cyclopropyl)propanoic acid, 2-(1-((1-methylbicyclo[3.1.0]hexan-2-yl)methyl)cyclopropyl)acetic acid, 2-(1-((7-methylspiro[2.4]heptan-4-yl)methyl)cyclopropyl)acetic acid, and 4-(7-methylspiro[2.4]heptan-4-yl)butanoic acid.

9. The method of claim 8, wherein the one or more off-note providing ingredient is selected from the group consisting of sweetener, artificial sweetener, beverage, chewing gum, nutraceutical, and pharmaceutical.

10. The method of claim 8, wherein the one or more off-note providing ingredient comprises an artificial sweetener selected from the group consisting of aspartame, acesulfame K, saccharin, sucralose, sodium cyclamate and mixtures thereof.

11. The method of claim 8, wherein the one or more off-note providing ingredient comprises a sweetener selected from the group consisting of including stevioside, swingle extract, glycyrrhizin, perillartine, naringin dihydrochalcone, neohesperidine dihydrochalcone, mogroside V, rubusoside, rubus extract, rebaudioside A and mixtures thereof.

12. The method of claim 8, wherein the one or more off-note providing ingredient comprises a consumable selected from the group consisting of cocoa; coffee; caffeine; theobromine; diketopiperazines; vitamins; amino acids; vitamin B; casein; soy protein; ibuprofen; salicylic acid; glucoronolactone; acetaminophen; dextromethorphan; naringin; taurine; macrolide; bioxin; erythromycin; paracetamol; acetylsalicyclic acid; cimetidine; ranitidine; amoxicillin; cephalosporins; quassia; propylene glycol; triacetin; potassium; zinc; loperamide; limonin; flavonoids; isoflavones; genistein; diadzein; polyphenol; catechin; epicatechin; mint oil; D-menthol; hydrolysed vegetable protein; bitter peptides; preservatives; benzoic acid; potassium sorbate; polysorbate 80; sodium lactate; potassium lactate; sodium benzoate; citric acid; quinine; urea contained in chewing gums; essential oils; thyme; sage; basil; mint; Maillard reaction products; cyclic amines made from pyrrolidine/glucose, alanine/xylose, proline/sucrose or alanine/xylose; beer; hops; humulone; trans-isohumulone; lupulone; hulupone and mixtures thereof.

* * * * *

SEQUENCE LISTING

<160> NUMBER OF SEQ ID NOS: 4

<210> SEQ ID NO 1
<211> LENGTH: 1113
<212> TYPE: DNA
<213> ORGANISM: Artificial
<220> FEATURE:
<223> OTHER INFORMATION: recombinant sequence of rat/human/HSV
<220> FEATURE:
<221> NAME/KEY: CDS
<222> LOCATION: (1)..(1113)

<400> SEQUENCE: 1

| | | | | | | | | | | | | | | | | |
|---|---|---|---|---|---|---|---|---|---|---|---|---|---|---|---|---|
| atg | gcc | gct | gtt | acc | tat | cct | tca | tcc | gtg | cct | acg | acc | ttg | gac | cct | 48 |
| Met | Ala | Ala | Val | Thr | Tyr | Pro | Ser | Ser | Val | Pro | Thr | Thr | Leu | Asp | Pro | |
| 1 | | | | 5 | | | | | 10 | | | | | 15 | | |
| ggg | aat | gca | tcc | tca | gcc | tgg | ccc | ctg | gac | acg | tcc | ctg | ggg | aat | gca | 96 |
| Gly | Asn | Ala | Ser | Ser | Ala | Trp | Pro | Leu | Asp | Thr | Ser | Leu | Gly | Asn | Ala | |
| | | | 20 | | | | | 25 | | | | | 30 | | | |
| tct | gct | ggc | act | agc | ctg | gca | gga | ctg | gct | gtc | agt | ggc | gaa | ttc | atg | 144 |
| Ser | Ala | Gly | Thr | Ser | Leu | Ala | Gly | Leu | Ala | Val | Ser | Gly | Glu | Phe | Met | |
| | | 35 | | | | | 40 | | | | | 45 | | | | |
| aca | act | ttt | ata | ccc | atc | att | ttt | tcc | agt | gtg | gta | gtg | gtt | cta | ttt | 192 |
| Thr | Thr | Phe | Ile | Pro | Ile | Ile | Phe | Ser | Ser | Val | Val | Val | Val | Leu | Phe | |
| | 50 | | | | | 55 | | | | | 60 | | | | | |
| gtt | att | gga | aat | ttt | gct | aat | ggc | ttc | ata | gca | ttg | gta | aat | tcc | att | 240 |
| Val | Ile | Gly | Asn | Phe | Ala | Asn | Gly | Phe | Ile | Ala | Leu | Val | Asn | Ser | Ile | |
| 65 | | | | | 70 | | | | | 75 | | | | | 80 | |
| gag | cgg | gtc | aag | aga | caa | aag | atc | tct | ttt | gct | gac | cag | att | ctc | act | 288 |
| Glu | Arg | Val | Lys | Arg | Gln | Lys | Ile | Ser | Phe | Ala | Asp | Gln | Ile | Leu | Thr | |
| | | | | 85 | | | | | 90 | | | | | 95 | | |
| gct | ctg | gcg | gtc | tcc | aga | gtt | ggt | ttg | ctc | tgg | gta | tta | tta | tta | aat | 336 |
| Ala | Leu | Ala | Val | Ser | Arg | Val | Gly | Leu | Leu | Trp | Val | Leu | Leu | Leu | Asn | |
| | | | 100 | | | | | 105 | | | | | 110 | | | |
| tgg | tat | tca | act | gtg | ttt | aat | cca | gct | ttt | tat | agt | gta | gaa | gta | aga | 384 |
| Trp | Tyr | Ser | Thr | Val | Phe | Asn | Pro | Ala | Phe | Tyr | Ser | Val | Glu | Val | Arg | |
| | | 115 | | | | | 120 | | | | | 125 | | | | |
| act | act | gct | tat | aat | gtc | tgg | gca | gta | acc | ggc | cat | ttc | agc | aac | tgg | 432 |
| Thr | Thr | Ala | Tyr | Asn | Val | Trp | Ala | Val | Thr | Gly | His | Phe | Ser | Asn | Trp | |
| | 130 | | | | | 135 | | | | | 140 | | | | | |
| ctt | gct | act | agc | ctc | agc | ata | ttt | tat | ttg | ctc | aag | att | gcc | aat | ttc | 480 |
| Leu | Ala | Thr | Ser | Leu | Ser | Ile | Phe | Tyr | Leu | Leu | Lys | Ile | Ala | Asn | Phe | |
| 145 | | | | | 150 | | | | | 155 | | | | | 160 | |
| tcc | aac | ctt | att | ttt | ctt | cac | tta | aag | agg | aga | gtt | aag | agt | gtc | att | 528 |
| Ser | Asn | Leu | Ile | Phe | Leu | His | Leu | Lys | Arg | Arg | Val | Lys | Ser | Val | Ile | |
| | | | | 165 | | | | | 170 | | | | | 175 | | |
| ctg | gtg | atg | ctg | ttg | ggg | cct | tta | cta | ttt | ttg | gct | tgt | caa | ctt | ttt | 576 |
| Leu | Val | Met | Leu | Leu | Gly | Pro | Leu | Leu | Phe | Leu | Ala | Cys | Gln | Leu | Phe | |
| | | | 180 | | | | | 185 | | | | | 190 | | | |
| gtg | ata | aac | atg | aaa | gag | att | gta | cgg | aca | aaa | gaa | tat | gaa | gga | aac | 624 |
| Val | Ile | Asn | Met | Lys | Glu | Ile | Val | Arg | Thr | Lys | Glu | Tyr | Glu | Gly | Asn | |
| | | 195 | | | | | 200 | | | | | 205 | | | | |
| atg | act | tgg | aag | atc | aaa | ttg | agg | agt | gca | gtg | tac | ctt | tca | gat | gcg | 672 |
| Met | Thr | Trp | Lys | Ile | Lys | Leu | Arg | Ser | Ala | Val | Tyr | Leu | Ser | Asp | Ala | |
| | 210 | | | | | 215 | | | | | 220 | | | | | |
| act | gta | acc | acg | cta | gga | aac | tta | gtg | ccc | ttc | act | ctg | acc | ctg | cta | 720 |
| Thr | Val | Thr | Thr | Leu | Gly | Asn | Leu | Val | Pro | Phe | Thr | Leu | Thr | Leu | Leu | |
| 225 | | | | | 230 | | | | | 235 | | | | | 240 | |
| tgt | ttt | ttg | ctg | tta | atc | tgt | tct | ctg | tgt | aaa | cat | ctc | aag | aag | atg | 768 |
| Cys | Phe | Leu | Leu | Leu | Ile | Cys | Ser | Leu | Cys | Lys | His | Leu | Lys | Lys | Met | |
| | | | | 245 | | | | | 250 | | | | | 255 | | |

-continued

```
cag ctc cat ggt aaa gga tct caa gat ccc agc acc aag gtc cac ata      816
Gln Leu His Gly Lys Gly Ser Gln Asp Pro Ser Thr Lys Val His Ile
        260                 265                 270 aaa gct ttg caa act gtg atc ttt ttc ctc ttg tta tgt gcc gtt tac      864
Lys Ala Leu Gln Thr Val Ile Phe Phe Leu Leu Leu Cys Ala Val Tyr
            275                 280                 285 ttt ctg tcc ata atg ata tca gtt tgg agt ttt ggg agt ctg gaa aac      912
Phe Leu Ser Ile Met Ile Ser Val Trp Ser Phe Gly Ser Leu Glu Asn
    290                 295                 300 aaa cct gtc ttc atg ttc tgc aaa gct att aga ttc agc tat cct tca      960
Lys Pro Val Phe Met Phe Cys Lys Ala Ile Arg Phe Ser Tyr Pro Ser
305                 310                 315                 320 atc cac cca ttc atc ctg att tgg gga aac aag aag cta aag cag act     1008
Ile His Pro Phe Ile Leu Ile Trp Gly Asn Lys Lys Leu Lys Gln Thr
                325                 330                 335 ttt ctt tca gtt ttg cgg caa gtg agg tac tgg gtg aaa gga gag aag     1056
Phe Leu Ser Val Leu Arg Gln Val Arg Tyr Trp Val Lys Gly Glu Lys
            340                 345                 350 cct tca tct cca tgc ggc cgc cag cct gaa ctc gct cct gaa gac ccg     1104
Pro Ser Ser Pro Cys Gly Arg Gln Pro Glu Leu Ala Pro Glu Asp Pro
        355                 360                 365 gaa gat taa                                                         1113
Glu Asp
    370

<210> SEQ ID NO 2
<211> LENGTH: 370
<212> TYPE: PRT
<213> ORGANISM: Artificial
<220> FEATURE:
<223> OTHER INFORMATION: Synthetic Construct

<400> SEQUENCE: 2

Met Ala Ala Val Thr Tyr Pro Ser Ser Val Pro Thr Thr Leu Asp Pro
1               5                   10                  15

Gly Asn Ala Ser Ser Ala Trp Pro Leu Asp Thr Ser Leu Gly Asn Ala
            20                  25                  30

Ser Ala Gly Thr Ser Leu Ala Gly Leu Ala Val Ser Gly Glu Phe Met
        35                  40                  45

Thr Thr Phe Ile Pro Ile Ile Phe Ser Ser Val Val Val Leu Phe
    50                  55                  60

Val Ile Gly Asn Phe Ala Asn Gly Phe Ile Ala Leu Val Asn Ser Ile
65                  70                  75                  80

Glu Arg Val Lys Arg Gln Lys Ile Ser Phe Ala Asp Gln Ile Leu Thr
                85                  90                  95

Ala Leu Ala Val Ser Arg Val Gly Leu Leu Trp Val Leu Leu Leu Asn
            100                 105                 110

Trp Tyr Ser Thr Val Phe Asn Pro Ala Phe Tyr Ser Val Glu Val Arg
        115                 120                 125

Thr Thr Ala Tyr Asn Val Trp Ala Val Thr Gly His Phe Ser Asn Trp
    130                 135                 140

Leu Ala Thr Ser Leu Ser Ile Phe Tyr Leu Leu Lys Ile Ala Asn Phe
145                 150                 155                 160

Ser Asn Leu Ile Phe Leu His Leu Lys Arg Arg Val Lys Ser Val Ile
                165                 170                 175

Leu Val Met Leu Leu Gly Pro Leu Leu Phe Leu Ala Cys Gln Leu Phe
            180                 185                 190

Val Ile Asn Met Lys Glu Ile Val Arg Thr Lys Glu Tyr Glu Gly Asn
```

```
                     195                 200                 205
Met Thr Trp Lys Ile Lys Leu Arg Ser Ala Val Tyr Leu Ser Asp Ala
    210                 215                 220

Thr Val Thr Thr Leu Gly Asn Leu Val Pro Phe Thr Leu Thr Leu Leu
225                 230                 235                 240

Cys Phe Leu Leu Leu Ile Cys Ser Leu Cys Lys His Leu Lys Lys Met
                245                 250                 255

Gln Leu His Gly Lys Gly Ser Gln Asp Pro Ser Thr Lys Val His Ile
            260                 265                 270

Lys Ala Leu Gln Thr Val Ile Phe Phe Leu Leu Leu Cys Ala Val Tyr
        275                 280                 285

Phe Leu Ser Ile Met Ile Ser Val Trp Ser Phe Gly Ser Leu Glu Asn
    290                 295                 300

Lys Pro Val Phe Met Phe Cys Lys Ala Ile Arg Phe Ser Tyr Pro Ser
305                 310                 315                 320

Ile His Pro Phe Ile Leu Ile Trp Gly Asn Lys Lys Leu Lys Gln Thr
                325                 330                 335

Phe Leu Ser Val Leu Arg Gln Val Arg Tyr Trp Val Lys Gly Glu Lys
            340                 345                 350

Pro Ser Ser Pro Cys Gly Arg Gln Pro Glu Leu Ala Pro Glu Asp Pro
        355                 360                 365

Glu Asp
    370

<210> SEQ ID NO 3
<211> LENGTH: 45
<212> TYPE: DNA
<213> ORGANISM: herpes simplex virus

<400> SEQUENCE: 3
tgcggccgcc agcctgaact cgctcctgaa gacccggaag attaa              45

<210> SEQ ID NO 4
<211> LENGTH: 144
<212> TYPE: DNA
<213> ORGANISM: rat

<400> SEQUENCE: 4
atggccgctg ttacctatcc ttcatccgtg cctacgacct tggaccctgg gaatgcatcc    60
tcagcctggc ccctggacac gtccctgggg aatgcatctg ctggcactag cctggcagga   120
ctggctgtca gtggcgaatt catg                                         144
```